US00PP08406P

United States Patent [19]

Trees

[11] Patent Number: Plant 8,406

[45] Date of Patent: Oct. 5, 1993

[54] NEW GUINEA IMPATIENS NAMED BSR-181 BRIGHT SCARLET

[75] Inventor: Scott C. Trees, Arroyo Grande, Calif.

[73] Assignee: George J. Ball, Inc., West Chicago, Ill.

[21] Appl. No.: 911,538

[22] Filed: Jul. 10, 1992

[51] Int. Cl.[5] ..... A01H 5/00
[52] U.S. Cl. ..... Plt./87.6
[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-181 Bright Scarlet is provided. This new cultivar was the result of a controlled breeding program wherein a plant designated BSR-12 (non-patented in the United States) was pollinated by a plant designated BSR-27 (non-patented in the United States). The new cultivar forms attractive very large bright scarlet blossoms combined with a strong basal branching character and a compact upright mounded growth habit and can be readily distinguished from the Aenea cultivar (U.S. Plant patent application pending).

1 Drawing Sheet

SUMMARY OF THE INVENTION

The present invention comprises a new and distinctive Impatiens plant, botanically known as New Guinea Impatiens, and hereafter referred to by the cultivar name BSR-181 Bright Scarlet.

The new cultivar is the product of a planned breeding program. More specifically, the breeding program which resulted in the production of the new cultivar was carried out in a controlled environment at Santa Maria, Calif., U.S.A. The female parent (i.e., the seed parent) was a plant designated BSR-12 (non-patented in the United States) which exhibits rose red blossoms with medium green foliage. The male parent (i.e., the pollen parent) was a plant designated BSR-27 (non-patented in the United States) which exhibits bright scarlet blossoms with medium green foliage having yellow-green variegation. The parentage of the new cultivar can be summarized as follows:

BSR-12×BSR-27.

The seeds resulting from the above pollination were sown and plantlets were obtained which were physically and biologically different from each other. Selective study during January, 1990 resulted in the identification of a single plant of the new cultivar. This plant had bright scarlet blossoms and initially was designated BSR-181.

It was found that the cultivar of the present invention:

(a) exhibits attractive very large bright scarlet blossoms which commonly measure approximately 7.5 cm. in diameter and approximately 7.25 cm. in length.
(b) exhibits a strong basal branching character, and
(c) exhibits a compact upright mounded growth habit.

Asexual reproduction of the new cultivar by terminal or stem cuttings taken during February, 1990 at Santa Maria, Calif., has demonstrated that the characteristics of the new cultivar as herein described are firmly fixed and are retained through successive generations of such asexual propagation.

The BSR-181 Bright Scarlet cultivar has not been observed under all possible environmental conditions to date. Accordingly, it is possible that the phenotype may vary somewhat with variations in the environment, such as temperature, light intensity, and day length.

When the new cultivar of the present invention is compared to the Aenea cultivar (U.S. Plant patent application pending), it is found that the new variety exhibits a compact upright mounded growth habit whereas the Aenea cultivar exhibits a more spreading mounded growth habit. Also, the flowering of BSR-181 Bright Scarlet cultivar is more profuse than that of the Aenea cultivar, and the flowers tend to be held well above the foliage.

When plant material of the BSR-181 Bright Scarlet cultivar is subjected to standard random amplified polymorphic DNA marker analysis (RAPD) using polymerase chain reaction (PCR) and a known unique set of DNA primers, it is found to exhibit a different fingerprint map when compared to that of the AENEA cultivar which confirms its genetic distinctiveness.

Plants of the new cultivar will be marketed under the Celebration trademark by George J. Ball, Inc.

BRIEF DESCRIPTION OF THE PHOTOGRAPH

The accomapnying photograph shows as nearly true as it is reasonably possible to make the same in a color illustration of this character, a typical specimen of an overall plant of the new cultivar. The plant was grown in a greenhouse at Arroyo Grande, Calif. U.S.A.

DETAILED DESCRIPTION

The chart used in the identification of colors described herein is The R.H.S. Colour Chart of The Royal Horticultural Society, London England. The color values were determined during the first week of January, 1992. the readings were taken at Arroyo Grande, Calif., U.S.A. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Strong basal branching.

*Habit of growth.*—Compact and upright mounded. A mature plant commonly measures approximagely 12 inches in height and approximately 15 inches in width.

*Foliage.*—The configuration is narrow and lanceolate. The leaves of the BSR-181 Bright Scarlet cultivar measure approximately 12 cm.×3 cm. while those of the Aenea cultivar measure approximately 9.5 cm×2.5 cm. The foliage of the BSR-181 Bright Scarlet cultivar is Green Group 139A. This can be compared to Green Group 137A for the Aenea cultivar, Also, the leaves of the BSR-181 Bright Scarlet cultivar are not as shiny as those of the Aenea cultivar. The stem color is light green, Green Group 135C, while that of the Aenea cultivar is Red Group 46A.

Flower description:

*Flowering habit.*—Freely flowering.

*Natural flowering season.*—Year-round in greenhouse environment.

*Flowers borne.*—Above foliage, arising from leaf axils.

*Flower color.*—Red Group 44B (abaxial) and Red Group 42B (adaxial). This can be compared to Red Group 42A (abaxial) and Red Group 43A for the Aenea cultivar.

*Quantity of flowers.*—Approximately 5 to 10 per stem.

*Number of petals.*—Five.

*Flower diameter.*—Approximately 7.5 cm. which can be compared to approximately 6.5 cm. for the Aenea cultivar.

*Nectary length.*—Approximately 7.25 cm. which can be compared to approximately 5.0 cm. for the Aenea cultivar.

*Nectary color.*—Red Group 47A which can be compared to Red Group 46A for the Aenea cultivar.

*Reproductive organs.*—The anthers are fused together forming one organ that surrounds the pistil. Generally, the anthers shed pollen prior to the stigma becoming receptive. The pollen color is cream-white, White Group 155D. The stigma color is White Group 155D and can be compared to White Group 155C exhibited by the Aenea cultivar. The ovary color is Yellow-Green Group 144D and can be compared to Yellow-Green Group 144B exhibited by the Aenea cultivar.

I claim:

1. A new and distinct cultivar of New Guinea Impatiens named BSR-181 Bright Scarlet, substantially as herein shown and described, which:

(a) exhibits attractive very large bright scarlet blossoms which commonly measure approximately 7.5 cm. in diameter and approximately 7.25 cm. in length, (b) exhibits a strong basal branching character, and (c) exhibits a compact upright mounded growth habit.

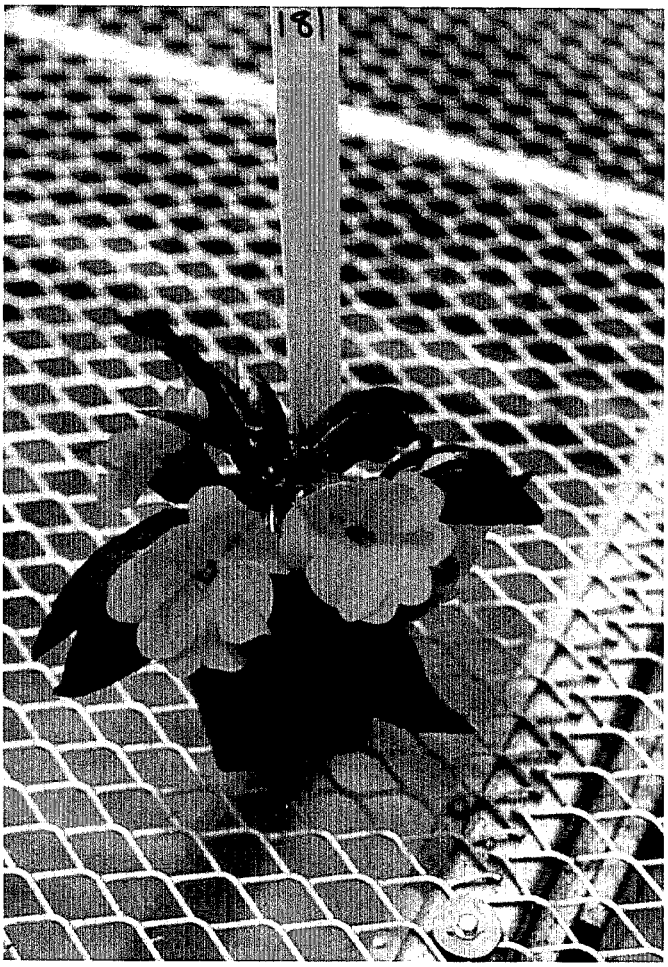

* * * * *